United States Patent [19]

Birchard

[11] Patent Number: 4,751,821

[45] Date of Patent: Jun. 21, 1988

[54] DIGITAL LINEAR ACTUATOR

[76] Inventor: William G. Birchard, 9710 Golf Links Rd., Tucson, Ariz. 85730

[21] Appl. No.: 717,570

[22] Filed: Mar. 29, 1985

[51] Int. Cl.$^4$ ............................................. F03G 7/00
[52] U.S. Cl. ......................................... 60/698; 60/527; 60/531; 91/167 R; 901/14; 901/15; 901/19
[58] Field of Search ................... 91/167; 60/527, 528, 60/698, 531; 92/48, 92; 901/2, 14, 15, 16, 17, 19, 22

[56] References Cited

U.S. PATENT DOCUMENTS

| | | | |
|---|---|---|---|
| 2,969,042 | 1/1961 | Litz et al. | 91/167 |
| 2,974,492 | 3/1961 | Gilovich | 91/167 X |
| 3,041,821 | 7/1962 | Lindberg, Jr. | 60/527 |
| 3,218,934 | 11/1965 | Daniels | 91/167 |
| 3,935,795 | 2/1976 | Hawley | 91/167 R X |

*Primary Examiner*—Allen M. Ostrager
*Attorney, Agent, or Firm*—Cahill, Sutton & Thomas

[57] ABSTRACT

A digital linear actuator includes a plurality of digital actuator cells each connected to the next in sequential fashion. Each of the digital actuator cells contracts or expands a predetermined amount along an expansion/contraction axis when it is actuated by a corresponding digital signal. Each digital actuator cell includes an inner portion containing a medium which expands or contracts in response to a digital signal. The inner portion is disposed within an outer portion that contracts in the direction of the axis in response to expansion of the inner portion, and expands in the direction of the axis in response to contraction of the inner portion. The device is useful in simulating the behavior of a muscle in a prosthetic device. Several embodiments of the invention are disclosed in which an arm can be extended to and retracted from a snake-like configuration. Another embodiment of the invention is disclosed which effectively simulates a shoulder and arm mechanism.

21 Claims, 7 Drawing Sheets

DIGITAL LINEAR ACTUATOR

BACKGROUND OF THE INVENTION

The invention relates to a "digital linear actuator", composed of a plurality of sequentially connected digital actuator cells each of which contracts in response to a corresponding digital signal.

Various mechanisms are known for producing controlled movement of a mechanical element or a connecting point thereof. For example, hydraulic and pneumatic cylinders are commonly used to produce forceful movement of arms and other mechanical elements of numerous mechanical, prosthetic, and/or robotic devices. Jackscrews which are rotated in a controlled fashion by stepper motors or servo motors in response to digital or analog control systems are widely used. Various cable and pulley assemblies and various chain and sprocket mechanisms also are commonly used to produce controlled movement of mechanical devices. Electrical solenoids and other electromagnetic devices also are commonly used to provide forceful movement of mechanical elements in response to suitable control signals. However, none of the above mechanical actuators and devices for producing forceful movement in a controlled fashion are really completely satisfactory for many of the applications in which they are commonly used. For example, in prosthetic devices in which the contraction of a human or animal muscle must be simulated, none of the above mechanical movement producing devices is entirely satisfactory because most of the devices mentioned above are too large in size and too great in mass to be ideal for controlling precise movement in prosthetic or robotic devices. All of the above mechanical movement-producing devices fail to provide a combination of features including smallness in size and mass, precision of controlling movement in response to digital signals, and very high force-producing capability that would be desirable in many prosthetic and robotic applications. Furthermore, most of the above mechanical movement-producing devices experience various other shortcomings in certain environments, for example, in environments in which there are corrosive ambient conditions or higher concentrations of abrasive and/or defect-causing dust or other minute particulates.

There is clearly a presently unfulfilled need for a type of device, referred to herein as a "digital linear actuator", which can produce precisely controlled, approximately linear movement of mechanical elements or connecting points in response to digital control information, and especially such a device that can fairly precisely simulate the contracting behavior of a muscle in response to the digtal control information, especially in a prosthetic or robotic device.

SUMMARY OF THE INVENTION

Accordingly, it is an object of the invention to provide a device which produces an approximately linear contracting movement and also can exert a relatively great force. in response to the state of a plurality of digital signal levels.

It is another object of the invention to provide a device which effectively simulates the contractile behavior of a muscle in response to the states of a plurality of digital signal levels and which is smaller in size and mass than prior movement-producing devices.

It is another object of the invention to provide a digital linear actuator which is suitable for use in prosthetic and robotic applications for moving of a mechanical arm or other mechanical element.

It is another object of the invention to provide a digital linear actuator cell which produces a repeatable, precise amount of contraction in a predetermined direction in response to expansion of a medium contained within the cell.

It is another object of the invention to provide such a digital linear actuator which can be actuated and "locked" into its controlled configuration for a reasonable length of time without draining significant amounts of power from an energy source.

It is another object of the invention to provide a digital actuator which can effectively simulate the movements of a human shoulder and arm.

It is another object of the invention to provide a digital actuator apparatus which can extend in a snake-like fashion through a predetermined path to control a utilization device.

Briefly described, and in accordance with one embodiment thereof, the invention provides a digital actuator cell including an outer portion that can expand or contract in the direction of an axis of the cell, and includes an inner portion that can expand or contract in accordance with the expansion or contraction of a medium contained in the inner portion, and a connecting element producing a fixed relationship between a first surface of the inner portion and a surface of the outer portion located on the opposite side of the inner portion, and a connection establishing a fixed relationship between an opposed second surface of the inner portion and a surface of the outer portion on the opposite side of the inner portion. In one described embodiment of the invention, a plurality of such digital actuator cells are sequentially connected together to provide a string thereof. In each digital actuator cell, the outer portion defines an outer chamber and the inner portion defines an inner chamber. The medium within each of the inner chambers responds to a separate digital signal level, respectively, causing a predetermined contraction of that digital actuator cell. In one described embodiment of the invention, the medium within each inner chamber is a polymer which expands rapidly when heated. A heating element is provided for heating the polymer in response to the digital signal level coupled to that digital actuator cell. In one described embodiment of the invention, the heating is accomplished by a Peltier device, which also acts to cool the polymer when the direction of the current through the Peltier device is reversed, causing contraction of the internal chamber and expansion of the outer chamber. In another embodiment of the invention, hydraulic or pneumatic tubing is coupled to the interior of the inner chamber and vented therefrom through valves that operate in response to a digital signal level to produce contraction or expansion of the outer chamber. In another embodiment of the invention, the medium is a controlled magnetic field, and a plurality of electromagnetic solenoids, each responsive to a different electrical signal, are connected in a series fashion to provide a digital linear actuator. In another described embodiment of the invention, a sealed, flexible tube encompasses all the digital actuator cells or elements of the entire digital linear actuator and expands and contracts therewith in response to various combinations of digital control signals applied to the respective actuator cells. The mechanical coupling between each of the digital actuator cells allows the digital linear actuator to be actuated while bending around corners and the like. In one embodiment of the invention, an outside source of coolant is pumped into the chemical medium within each inner chamber to produce contraction thereof and thereby relax the individual digital actuator cells and allow expansion of the digital linear actuator. The digital linear actuator is used to simulate the contractile behavior of a muscle in a prosthetic or robotic device and to produce precise, approximately linear movement of a connecting point of the prosthetic or robotic device relative to a reference connecting point or another connecting point, in response to various values of the digital word comprising all of the digital control signal levels.

In a presently preferred embodiment of the invention, a pneumatic tube couples high pressure air into a first one of the digital actuator cells through a steel tube that is anchored with respect to an outer housing having an open end into which an inner housing slidably moves. The steel tube passes slidably through a hole in an inner end cap of the inner chamber housing and is connected to a movable piston within the inner housing. A smaller diameter steel tube extends slidably through a hole through the piston and is rigidly attached to the opposite wall of the inner chamber housing. A continuous pneumatic passage extends through the piston rod and through the inner tube through a passage that extends through the wall of the inner chamber housing and passes the high pressure air into a flexible tubular coupling that conducts the high pressure air source through the first digital actuator cell to an essentially identical second digital actuator cell. A first valve opens in response to a digital "contract" signal to feed high pressure air through a passage in the wall of the inner chamber housing into a region or inner expansion chamber between the cover plate and the piston, causing that inner expansion chamber to expand, pushing the piston toward the opposite wall, and causing the outer tube to pull the outer chamber housing slidably over the surface of the inner chamber housing, thereby causing the digital actuator cell to fully contract to a dimension established by the inner dimensions of the inner housing. An air vent hole behind the piston relieves pressure between the piston and the back wall of the inner chamber housing as expansion of the inner expansion chamber and contraction of the digtal actuator cell occur. A second valve is opened in response to a "relax" signal to vent the pressure from the inner expansion chamber. In this pneumatic embodiment of the invention, a single high pressure source provides power for actuating all of the digital actuator cells comprised in a digital linear (or non-linear) actuator. This embodiment of the invention has the advantage that each actuator cell can be "locked" into its contracted or release configuration by simply causing both valves in communication with the inner expansion chamber to be closed once the desired contracted or relaxed configuration is achieved, even if the high pressure air source is then turned off. This allows the high pressure air source to be used for other purposes, for example, to actuate other similar digital linear actuators used to simulate other muscle-like configurations. In a somewhat similar embodiment of the invention, an explosive gas rather than air, is supplied from a source common to all of the digital actuator cells in a digital linear actuator. Each digital actuator cell includes an injector by means of which a charge of the explosive gas can be injected into the inner expansion chamber in response to a "contract" signal. After a slight delay, an electrical spark or other ignition means is actuated in response to the same "contract" signal, producing an explosion in the inner expansion chamber, causing selected cells of the digtal linear actuator to contract. In one described embodiment of the invention, a snake-like digital linear actuator arm is described in which a plurality of "major" digital linear actuators are each capable of being pivoted with respect to the adjacent one, and wherein at least three "minor" digital linear actuators are connected to control the amount that each major digital linear actuator pivots relative to the previous one. A utilization device connected to the distal end of the snake-like arm is controlled to perform a predetermined function after it has been carried through a predetermined path by the snake-like arm. The major digital linear actuators in this embodiment of the invention are composed of digital actuator cells that are capable of forceful expansion and contraction. In another embodiment of the invention, a plate that is connected to a stationary reference can be raised, lowered, and moved forward and backward, and can also be pivoted in a manner that roughly simulates movement of a human shoulder. Attached to the plate is an arm that is pivotally connected thereto, the amount of pivoting being controlled by at least three digital linear actuators that are pivotally anchored to the plate and are also connected to a ring plate supported by a bearing through which the arm extends and which allows the arm to rotate. Another digital linear actuator has one end anchored to a peripherial porting of the ring plate and also has another end attached in fixed relationship to the arm to effectuate its rotation. A second arm of similar structure is pivotally connected to the distal end of the first arm.

DESCRIPTION OF THE INVENTION

Figure 1:
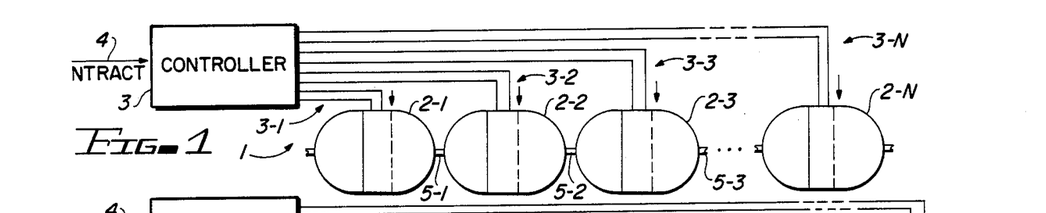
FIG. 1 is a schematic diagram illustrating a digital linear actuator of the present invention, in its fully contracted state.
Figure 2:
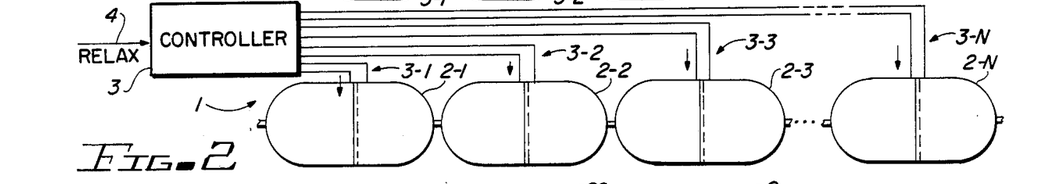
FIG. 2 is a diagram of the digital linear actuator of FIG. 1 in its completely relaxed state.

Referring to FIGS. 1 and 2, digital linear actuator 1 includes N digital actuator cells 2-1, 2-2 . . . 2-N. Each of the actuator cells has an end connector by means of which it is connected to the adjacent actuator cells. Reference numerals 5-1, 5-2, and 5-3 indicate such connectors. The extreme ends of the digital linear actuator are connected to suitable mechanical elements, for example to connecting elements of a robotic device or a prosthetic device or an anchor device (not shown).

Each actuator cell has two input terminals, designated by reference numerals 3-1, 3-2 . . . 3-N in FIGS. 1 and 2. These terminals can be electrical terminals, hydraulic terminals, or fluid (liquid or gas) terminals, as subsequently explained, for conducting electrical or fluid signals, respectively. If a suitable "signal" having a first level or state is applied between the input terminals of a particular actuator cell, that cell will be in a "relaxed" or expanded configuration with respect to its longitudinal axis, as illustrated in FIG. 2. If an opposite state or level is applied between the input terminals, the actuator cell contracts a precise predetermined amount.

In FIG. 1, each of the actuator cells is illustrated in its contracted configuration. If the input signal to the actuator cell is again changed back to its original state, the actuator cell will again "relax", i.e., expand forcefully back to its original state.

In FIGS. 1 and 2, reference numeral 3 designates a controller that responds to an input signal, which can be a "relax" (or "expand") signal or a "contract" signal, and generates an appropriate digital signal to the input terminals of each of the respective actuator cells to produce a net contraction or expansion between the end connectors of the digital linear actuator 1.

The "contract" or "relax" signal applied to input 4 can be an analog signal or a digital signal. If it is an analog signal, a suitable analog-to-digital converter device within controller circuit 3 can generate digital "contraction" signals which then are applied to the input terminals of only a certain number of the actuator cells of the digital linear actuator 1, depending upon the magnitude of the "contract" signal on input 4. Thus, it can be seen that the amount of contraction of the digital linear actuator 1 is an essentially "linear" function of relaxation of the digital linear actuator 1 can be similarly controlled. The expansion or contraction of the digital linear actuator 1 is "linear" in the sense that each actuator cell of the digital linear actuator contracts the same amount in response to a respective digital signal applied thereto. (Of course, a digital non-linear actuator in which some actuator cells contract by different amounts than others in response to the digital signals applied respectively thereto can be provided.)

Figure 3:
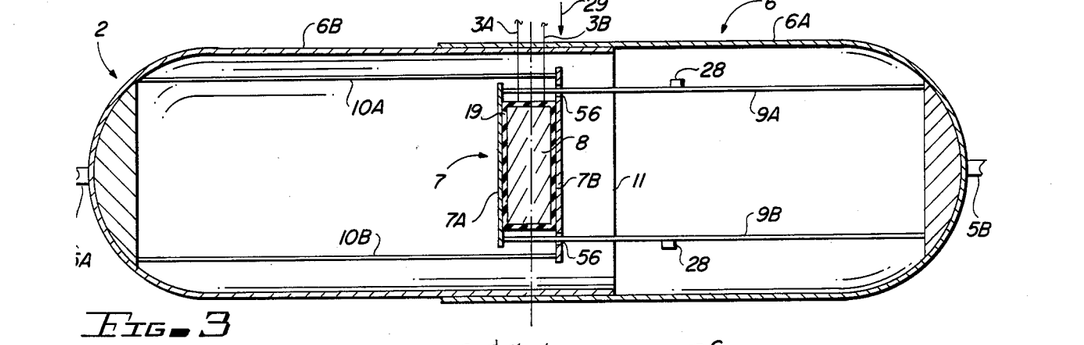
FIG. 3 is a section view illustrating the inner and outer chambers of an individual digital actuator cell of one embodiment of the invention.
Figure 4:
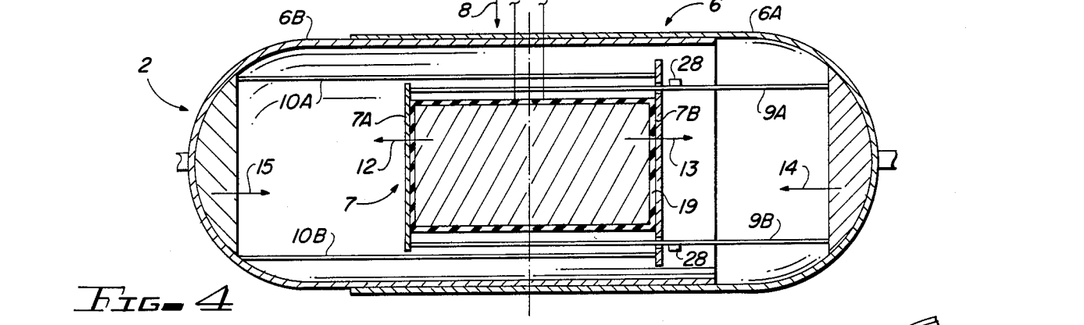
FIG. 4 is a section view diagram useful in explaining the operation of the digital actuator cell of FIG. 3.
Figure 5:
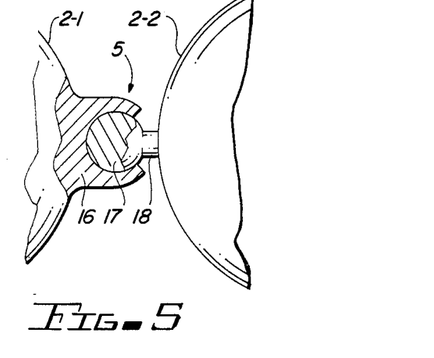
FIG. 5 is a partial cutaway diagram illustrating one type of mechanical coupling between individual digital actuator cells.

Next, the details of a number of different actuator cells will be described. Referring first to FIGS. 3 and 4, actuator cell 2 includes an outer chamber 6 and an inner chamber 7. Inner chamber 7, is hereinafter occasionally referred to as an "inner expansion chamber", even though it actually can either expand or contract. Inner expansion chamber 7 includes a rigid left wall 7A and a rigid right wall 7B and an expandable sealed liner 19 that is bounded at its left and right ends by walls 7A and 7B, and on its sides is bounded by a pair of cylindrical, telescoping walls that are respectively attached to left end 7A and right end 7B.

Actuator cell 2 includes an outer chamber which is designated by reference numeral 6. The outer chamber 6 is bounded by an outer section 6A and an inner section 6B which slides into the recess of section 6A in a telescoping fashion. A coupling element 5B is connected to the right end of the wall bounding outer chamber 6 and a coupling element 5A connected to the left end of section 6B bounding outer chamber 6 for coupling actuator cell 2 in series with other like actuator cells.

A medium 8 is contained within the liner 19 of inner chamber 7. Medium 8 is caused to expand as a result of an input signal 29 applied to actuator cell 2 by means of input conducting elements 3A and 3B. As subsequently explained, the input conducting elements 3A and 3B can be electrical conductors or fluid conductors or gas conductors, and the term "signal" encompasses a suitable electrical signal level or a suitable fluid flow rate or pressure.

At any rate, when a suitable input signal 29 is applied, the medium 8 expands, causing the left end 7A and predetermined amount in the directions of arrows 12 and 13, respectively. The lengths of the telescoping sides of inner chamber 7 and suitable stops 28 on pull rods 9A and 9B or the abutment of the walls of the inner chamber can be used to provide precise, repeatable limits of the expansion and contraction of actuator cell 2.

Pull rod 9A extends through an opening 56 in right end 7B, and connects left end 7A to the right end of section 6A of the wall of outer chamber 6. Similarly, pull rod 9B connects the lower end of left wall 7A to the right end of chamber wall 6A. Similarly, pull rods 10A and 10B connect right end wall 7B of inner chamber 7 to the left chamber enclosure 6B of actuator cell 2. Thus, it can be seen that the above-mentioned expansion of medium 8, causing expansion of inner chamber end 7A and 7B in the directions of arrows 12 and 13, respectively, causes contraction of outer chamber sections 6A and 6B in the direction of arrows 14 and 15. The stops 28 precisely limit the amount of expansion caused by a "contract" signal 8 applied to the input terminals 3A and 3B. Reversal of the input signal, i.e., application of a "relax" signal allows or (depending on the expansion/contraction medium) forces the actuator cell to expand back to its initial length, as shown in FIG. 3.

Figure 6:
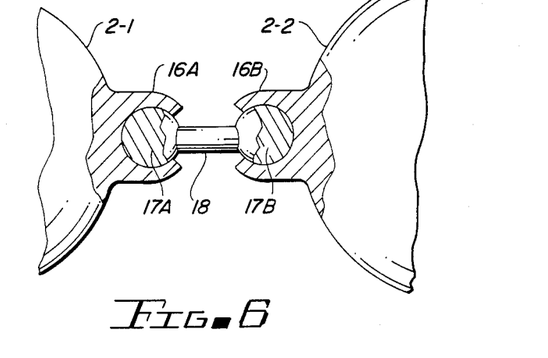
FIG. 6 is a partial cutaway diagram illustrating another type of pivotal coupling between individual digital actuator cells of a digital linear actuator.

FIG. 4 illustrates one type of end coupling element for the actuator cells 2, in which actuator cell 2-1 includes a socket 16, and actuator cell 2-2 includes a ball 17 which fits into socket 16. Ball 17 is connected to the end of actuator cell 2.1. Reference numeral 5 generally designates the illustrated end coupling element. FIG. 6 discloses another variation in which all of the actuator cells such as 2.1 and 2.2 have end sockets such as 16A and 16B, each of which receives a ball 17A and 17B, respectively that are rigidly connected together by means of a rod 18.

Figure 7:
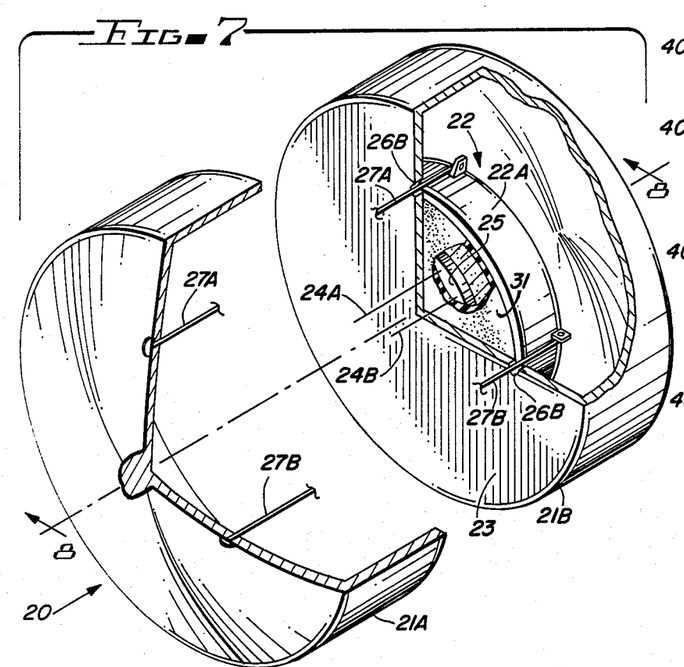
FIG. 7 is a partial cutaway exploded view of one digital actuator cell of the present invention.

Referring next to FIG. 7, a different actuator cell 20 is shown which includes only one set of pull rods 27A and 27B that connect the right end 22A of an inner expansion chamber 22 to the left end of an outer chamber shell section 21A. The left end of inner expansion chamber 22 is integral with a plate 23 that is attached to the side walls of an inner shell section 21B that extends inside the recess formed by left outer chamber shell 21A. The input terminals 24A and 24B are electrical signal terminals that are applied to a heating element 25 located inside inner chamber 22, which heats expansion medium 31 to cause it to expand. The structure and operation can better be described with reference to FIGS. 8 and 9, which are section views taken along section line 8—8 of FIG. 7.

Figure 8:
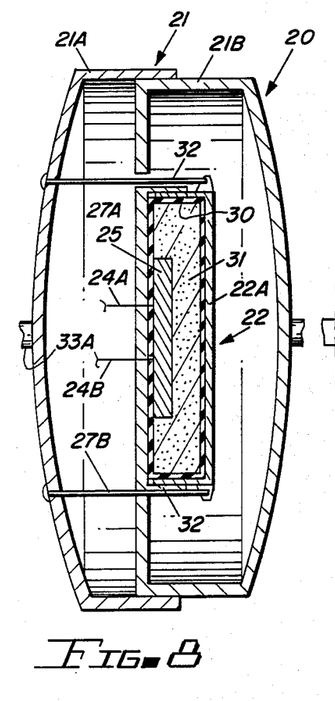
FIG. 8 is a section view along section line 8—8 of FIG. 7.
Figure 9:
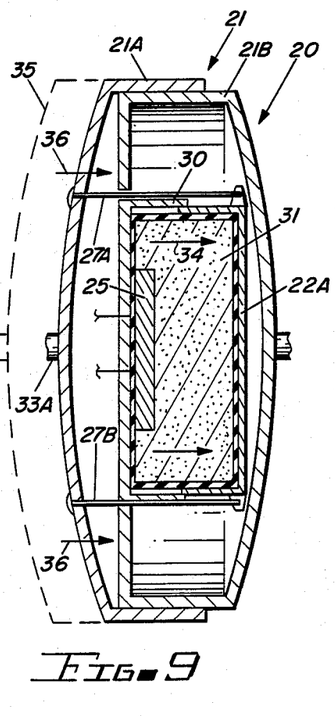
FIG. 9 is a section view similar to FIG. 8 showing the digital actuator cell of FIG. 7 in its actuated or contracted state.

Heating element 25 can be a Peltier device, which has the characteristic that when current through input terminals 24A and 24B flows in one direction, it operates as a heating element, and when the direction of the current is reversed, it acts as a cooling element. Heating of the medium 31 causes it to expand to roughly twice its normal dimension, and cooling it causes it to contract back to its initial volume.

When the input signal causes Peltier device 25 to heat expansion medium 31, this causes the left end 22A of inner chamber 22 to move in the direction of arrows 34, pulling pull rods 27A and 27B to the left. The left ends of pull rods 27A and 27B are connected to the outer left chamber shell 21A, causing it to move in the direction of arrows 36 from its initial configuration indicated by dotted line 35. The left end of the inner expansion chamber 22 is held in fixed relationship to the right end shell section 21B of the outer chamber 21 by causing plate 23 to be rigidly attached to the side walls of right outer chamber housing 21B.

Figure 10:
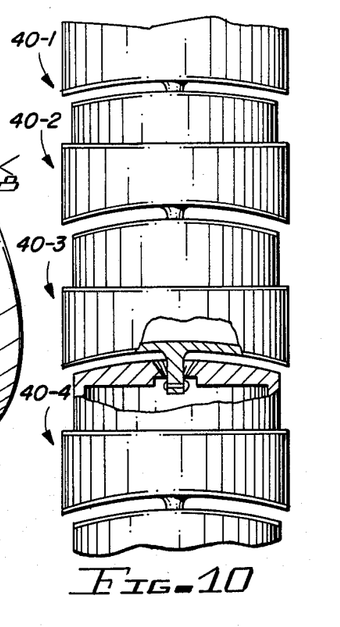
FIG. 10 is a diagram illustrating several cells of another digital linear actuator in accordance with the present invention.

FIG. 10 shows a portion of a digital linear actuator including a number of series connected actuator cells 40-1, 40-2, 40-3, and 40-4 with different shell configurations which are altered slightly from that shown in FIG. 7-9. This structure would be suitable where less bending and twisting of the digital linear actuator is needed than would be acceptable for the outer shell configuration shown in FIG. 7-9, the latter configuration allowing more bending of the digital linear actuator formed thereby.

Figure 11:
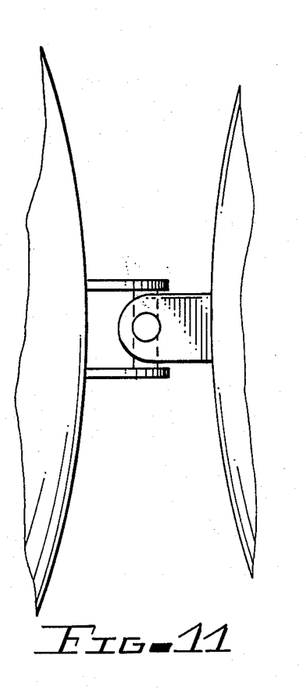
FIG. 11 is a diagram illustrating another type of coupling that can be used between digital actuator cells.

FIG. 11 shows the use of a conventional U-joint as the coupling element between successive actuator cells.

Figures 12, 13, 14, 15, 16:
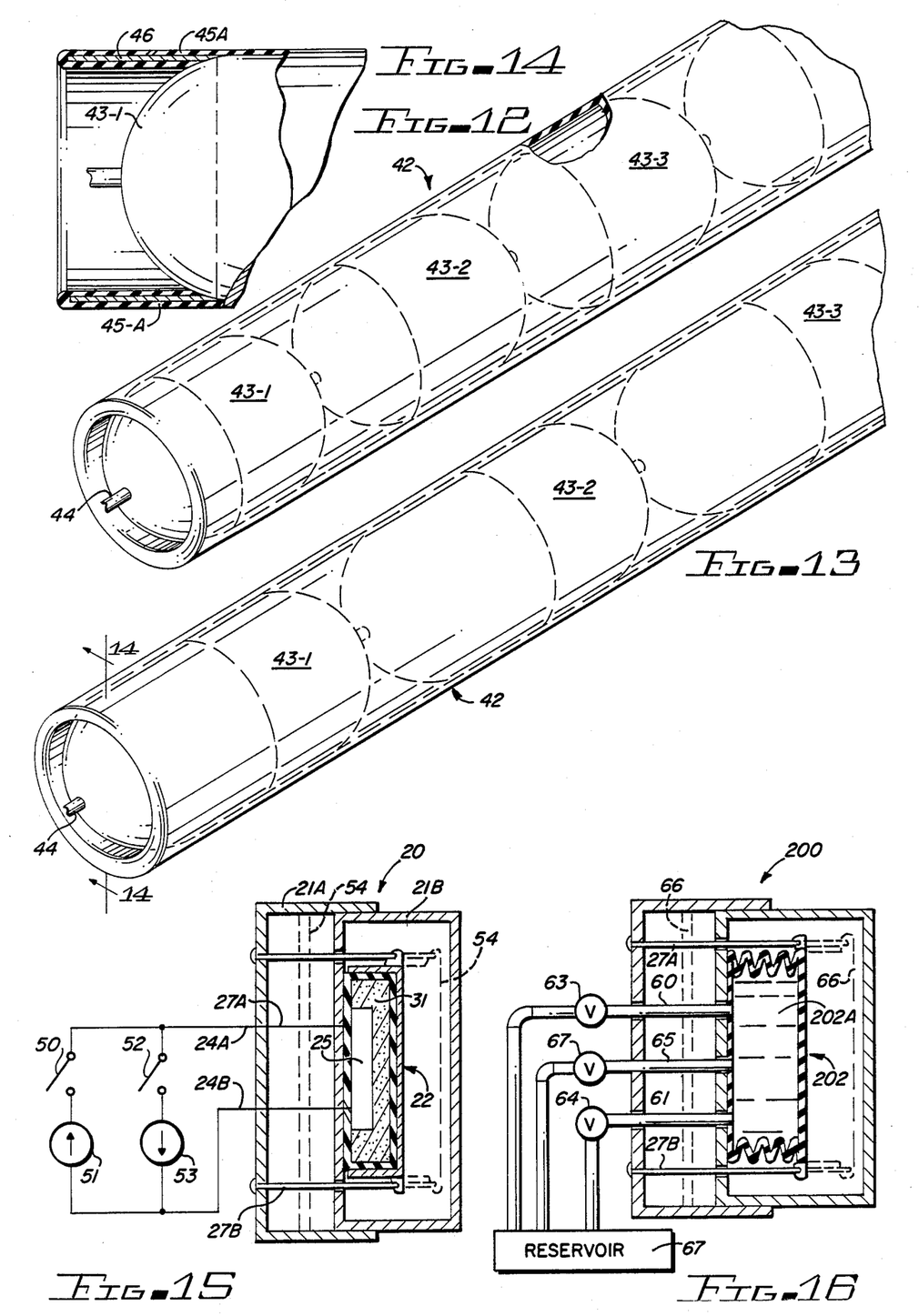
FIG. 12 is a perspective view illustrating a sleeve encompassing a contracted digital linear actuator.
FIG. 13 is a partial perspective view illustrating a flexible sleeve encasing a digital linear actuator in accordance with the invention.
FIG. 14 is a section view along section line 14—14 of FIG. 13.
FIG. 15 is a section view schematic diagram useful in explaining the operation of a digital actuator cell with a chemical expansion medium in the inner expansion chamber and a Peltier device in the inner expansion chamber for controllably heating and cooling the chemical expansion medium.
FIG. 16 is a section view in which hydraulic or pneumatic pressure is used to produce expansion of the inner chamber and hence contraction of the outer chamber of a digital actuator cell.

Referring next to FIGS. 12-14, another embodiment of the invention is shown in which a digital linear actuator 42 includes a plurality of individual actuator cells 43-1, 43-2, etc., coupled together as indicated in FIG. 1, wherein the controller and control terminals have been omitted for convenience. However, a flexible, stretchable outer sleeve 45 encapsulates all of the actuator cells therein and seals them from outside environmental influences. In FIG. 13, the sealed digital linear actuator is shown in its relaxed state. Sleeve 45 expands to accomodate the relaxed configuration of the individual actuator cells. In FIG. 12, at least some of the actuator cells are contracted, and the sleeve 45 shrinks accordingly.

FIG. 14 illustrates a useful technique for attaching the ends of the sleeve 45 so as to form a seal with the actuator cells at the extreme ends of the digital linear actuator 42. For example, the left end actuator cell 43-1 has a cylindrical flange 46 attached thereto. The end of the cylindrical sleeve 45 extends around the edge and into the interior of the region bounded by the cylindrical flange 46, an d is adhesively attached thereto to form a seal. This configuration has the advantage that the sleeve 42 protects the individual actuator cells from the influence of dirt, dust, or corrosive ambients.

If required, it would be possible to provide heating or cooling fluid in the space between the inner surface of the sleeve 42 and the outer surfaces of the actuator cells so that the cooling medium could, by thermal conduction to the inner chamber, cause contraction of the expansion medium, while small resistive heater elements actuated by electrical signals could rapidly provide enough heat to cause expansion of the expansion medium.

Referring now to FIG. 15, a current source 51 can be connected by a switch 50 between electrical input conductors 24A and 24B which are connected to Peltier device 25. When switch 50 is closed, switch 52 is open, producing a current through Peltier device 25 that causes it to rapidly heat the expansion medium 31, which can be an isoprene material, manufactured by Madison, Coleman & Bell Chemicals, part No. IX325-3. This will cause rapid expansion of medium 31, causing contraction of the actuator cell 20 from its initial configuration to the configuration indicated by dotted lines 54. To cause the actuator cell 20 to contract or relax, switch 50 is opened and switch 52 is closed, reversing the direction of the current flow and causing Peltier device 25 to cool the expansion medium 31 cools, causing it to contract to its initial volume and allowing the actuator cell 20 to relax to its initial configuration.

FIG. 16 shows an alternate configuration in which a fluid from a reservoir 65 is passed in through valve 63 and out through valve 64 to control the temperature of a medium inside inner expansion chamber 202. Alternatively, pressurized fluid or gas is provided in reservoir 65 and valves 63 and 64 of each cell are controlled in response to digital signals to cause the inner expansion chamber 202A to forcefully expand or contract. External fluid or electrical control signals can be applied to valves 63 and 64 to control whether pressurized fluid from reservoir 65 is admitted into and retained in inner expansion chamber 202A to cause expansion thereof, and hence contraction of the cell 200, or whether pressurized fluid is drawn out of, or allowed to escape from inner expansion chamber 202A, allowing the cell 200 to relax. Yet another alternative is to control valves 63 and 64 so as to admit or inject two substances into inner expansion chamber 202A, which then react and expand to cause expansion of inner expansion chamber 202A, and hence contraction of the cell 200; valve 67 then can be opened to allow venting of inner expansion chamber 202A through tube 66 to allow the cell to relax.

Figure 17:
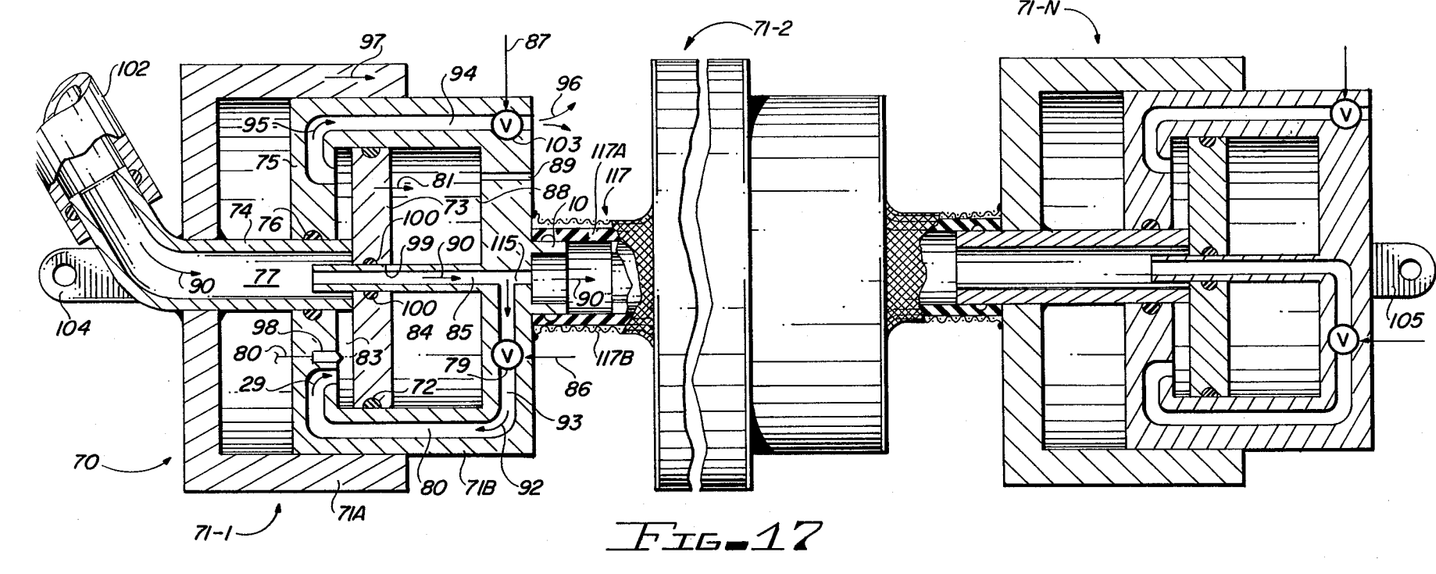
FIG. 17 is a diagram illustrating another embodiment of the invention in which a single source of high presure gas is used as the medium which causes expansion of the inner chamber and contracting of the outer chamber of each digital actuator cell of one entire digital linear actuator.

FIG. 17 illustrates a practical presently preferred embodiment of the invention which is pneumatically operated. The digtal linear actuator 70 shown in FIG. 17 includes a plurality of identical actuator cells 71-1, 71-2, . . . 71-N (collectively referred to by reference numeral 71) connected in series. Each of the actuator cells 70 includes an outer chamber housing 71A and an inner chamber housing 71B. Inner chamber housing 71B telescopes into outer chamber housing 71A, as shown. An end plate 75 is rigidly attached to the open end of the region bounded by housing 71B.

A cylindrical piston 73 is disposed within housing 71B and end plate 25, and is peripherally sealed by means of an O-ring 72. A piston rod 74 is attached to piston 73 and extends through an opening 76 in end plate 75.

An inner tube 84 extends slidably through a hole 99 in piston 73, and extends to the left into the interior of tubular piston rod 74. O-rings 100 provide an airtight seal. Pressurized gas or air designated by arrows 90 pass from passage 77 in piston rod 74 through passage 85 of inner tube 84 and also through an opening 115 in the left wall of housing 71B to a protruding connector 101, and also through a flexible, airtight coupling 117 into the piston rod 74 of the adjacent, essentially identical actuator cell 71-2. In this fashion, pressurized air from an external source is fed from a tube 102 to all of the digital actuator cells 71-1. . .71-N.

The flexible, airtight coupling 117 can include a reinforced rubber tube or the like designated by reference numeral 117A to provide an airtight coupling between the connector flanges 101 and a length of woven steel hose 117B attached to the left wall of cell 71-2 and the right wall of cell 71-1 by welding on the like.

A passage 93 extends from passage 85 in inner tube 84 into inner expansion chamber 83 between the left side of piston 73 and the cover plate 75. A air valve 79 is controlled in response to a digital signal 86.

Inner expansion chamber 83 also opens into a venting passage 94 that it passes through the wall of inner housing 71B through a valve 103 that is actuated by the logical complement of the digital signal that controls valve 79, and on to the outside atmosphere.

In operation, assuming piston 73 is at its left-most position so that inner expansion chamber 83 has its lowest volume, a digital "contract" signal is applied to terminal 86, causing valve 79 to open. Meanwhile, a corresponding signal on conductor 87 is applied to valve 103, keeping it closed so that no air can escape from inner expansion chamber 83. Open valve 79 then allows pressurized air from the external source to pass into inner expansion chamber 83, as indicated by arrows 92. This causes piston 73 to move to the right, as indicated by arrow 81. Air in chamber 88 is exhausted through vent hole 89 as piston 73 moves to the left to its right-most position. This, of course, causes piston rod 74 to also move to the right, causing outer housing 71A to move to the right in the direction indicated by arrow 97, thus causing digital actuator cell 71A to contract by a predetermined amount in response to the contract signal applied to terminal 86.

In accordance with an important aspect of the present invention, the "contract" signal 85 can be removed from terminal 86, causing valve 79 to close, thereby trapping the pressurized air in inner expansion chamber 83, causing actuator cell 71A to "hold" or be "locked into" its contracted configuration, even if the air pressure in passages 77, 85, etc. is removed.

In order to cause the actuator cell 71A to relax, a "relax" signal is applied to terminal 87, causing valve 103 to open, thereby venting the pressure in inner expansion chamber 83, and allowing the piston to be pulled back to its left-most position. (Typically, the device connected to the extreme end connectors 104 and 105 will provide an external countering force which will expand the digital linear actuator 70 when the "relax" signals are applied to all of the cells thereof.)

The digital actuator cell 70-1 can be made to forcefully expand, as well as forcefully contract, by providing a value that is entirely similar to valve 79 that controllably routes the pressurized gas or fluid from passage 77 into chamber 88 instead of chamber 83, forcing piston 73 to move to the left, instead of to the right, provided, however, that a suitably controlled valve is provided in series with the passage 89. These slight modifications make the digital actuator cell 71-1 suitable for applications where forceful expansion and forceful contraction are needed, as in the subsequently described embodiments of the invention in FIGS. 19, 20, and 21.

Thus, it can be seen that the digital linear actuator 70 of FIG. 17 can provide a precisely controlled amount of contraction in response to "contract" signals applied to some or all of the individual actuator cells 71-1, 71-2, etc. with a single, common source of pressurized air supplying the energy required for each actuator cell 71 to contract, and can be easily "locked" into a particular configuration, with the pressurized source removed.

In FIG. 17, reference numeral 98 designates a spark plug or other similar ignitor device that is responsive to the contract signal applied to terminal 80 for a slightly modified embodiment of the invention in which reference numeral 79 designates a gas charge injector. In this embodiment of the invention, instead of supplying compressed air or gas of a neutral variety, a combustible gas or gas mixture is conducted through the common passages 77, 85, etc. A "contract" signal applied to terminal 86 causes the injector of a particular actuator cell to inject a charge of combustible gas into the inner expansion chamber, and, in response to the same signal, the ignitor device 98 ignites the charge, causing the piston 73 to move to the left as the inner expansion chamber 83 expands, causing the actuator cell to contract.

Figure 18:
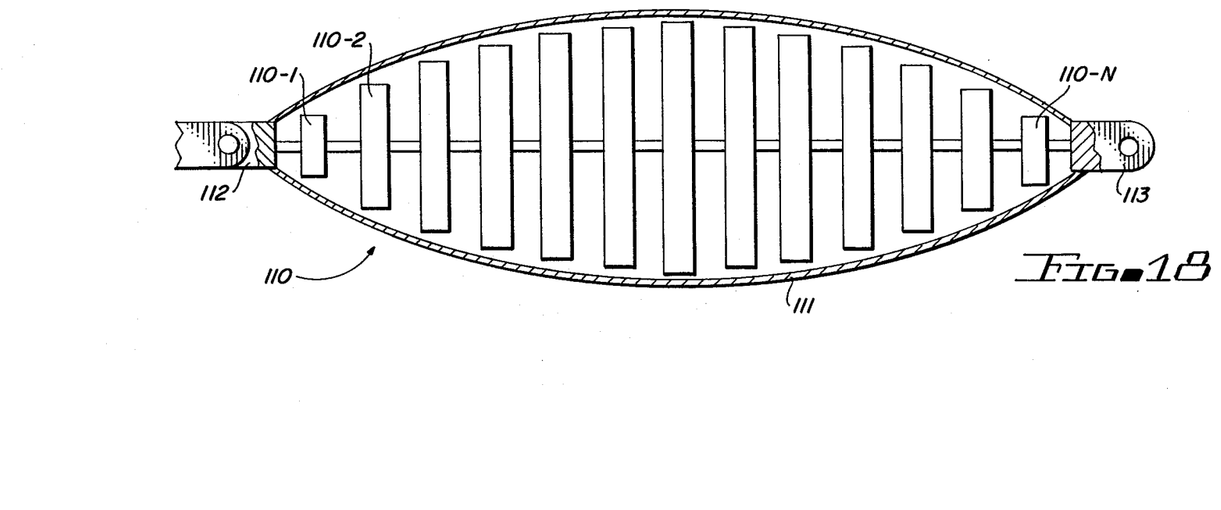
FIG. 18 is a diagram illustrating a digital linear actuator composed of varying sizes of digital actuator cells.

Referring next to FIG. 18, reference numeral 110 designates a non-linear digital actuator which is a variation of the earlier described digital linear actuators in which the individual actuator cells 110-1, 110-2. . .110-N are of varying sizes, both as to strength and contraction distance, as is the case in many animal muscles. Reference numeral 110 designates a protective sheath. Reference numerals 112 and 113 designate end connectors. This configuration has the advantages of allowing certain actuator cells having greater diameters and contractible lengths to be actuated to provide rapid, powerful contraction of the non-linear digital actuator 110. Then, other smaller diameter actuators can be actuated to provide more refined, precise contraction of non-linear digital actuator 110. The digital control signals are omitted from the illustration of FIG. 18, as they can be any of the gas, liquid, or electrical digital control signals previously mentioned, and also can be light signals conducted by optical fibers.

Figures 19, 19B:
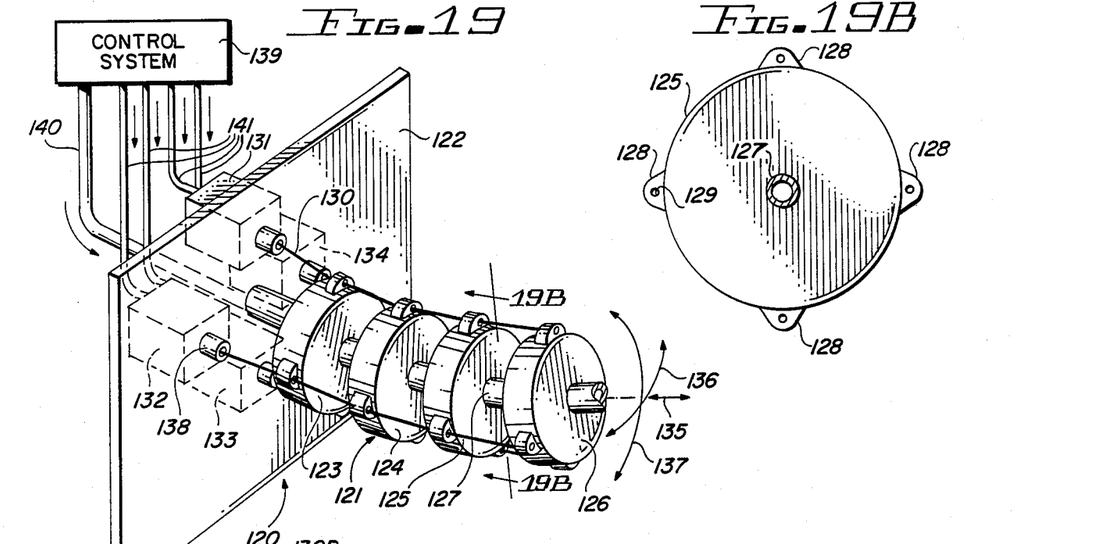
FIG. 19 is a partial perspective view of a snake-like digital linear actuator arm that can be extended through a predetermined path.
FIG. 19B is a section view taken along section line 19B—19B of FIG. 19.

Referring next to FIG. 19, a robotic apparatus 120 includes an arm 21, which, for lack of a better term of art, will be referred to herein as "snake arm" 121. Snake arm 121 is pivotally attached to stationary plate 122, and is controlled in response to a control system 139, which provides suitably pressurized fluid via tubing 140 to a plurality of relatively large "major DLAs" (digital linear actuators) 123, 124, 125, 126, etc. The outermost or distal major DLA (not shown) has attached to it a utilization mechanism such as one shown at the distal end of the arm shown on FIG. 20.

Control system 139 also supplies pressurized fluid or the like via conduits 141 to each of four minor digital linear actuator systems 131, 132, 133, and 134, that are each anchored to the back side of stationary plate 122.

Each of the major DLAs 123, 124, etc., has a capability of forcefully expanding and forcefully contracting in response to electrical control signals routed through a cable (not shown) to each of the major DLAs. Each of the minor DLA systems, such as 131, 132, etc., includes as many minor DLAs as there are major DLAs. Each minor DLA is connected by means of a plurality of cables 130 to a corresponding one of the major DLAs.

Figures 19A, 22A:
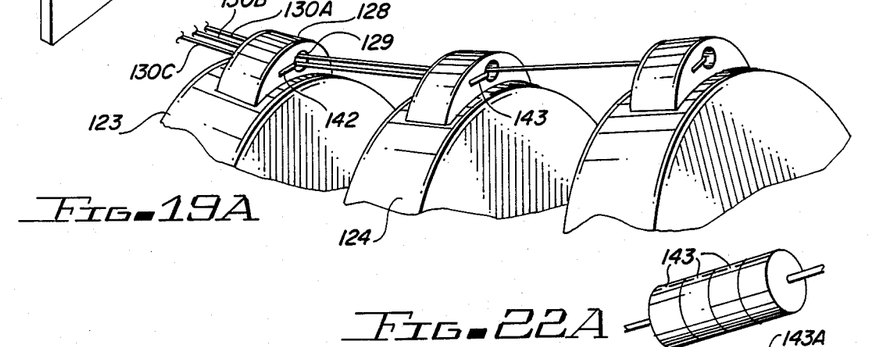
FIG. 19A is an enlarged partial perspective drawing useful in explaning the embodiment of FIG. 19.
FIGS. 22A-22D are perspective diagrams useful in explaining the operation of the digital linear actuators in the embodiments of FIGS. 20 and 21.

Each of the major DLAs includes four tabs 128, each having a guide hole 129 therein. Each of the major DLAs is pivotally connected by a structure similar to the one designated by reference numeral 117 in FIG. 17, which resists compression or expansion, but allows pivoting of one major DLA relative to the prior one. The cables 130 in FIG. 19 include a number of individual cables such as 130A, 130B, and 130C in FIG. 19A. Each of the cables, which are collectively referred to by reference numeral 130, is anchored to a separate one of the tabs 128 of the successively positioned major DLAs. Each of the individual cables 130A, 130B, etc., passes through the guide holes 129 of one or more of the major DLAs until they reach the one to which they are anchored. In FIG. 19A, reference numerals 142 and 143 designate anchoring points of individual cables.

Figure 22B:
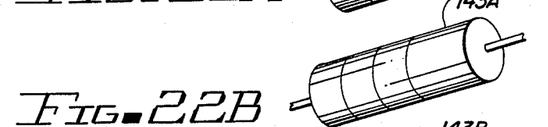
Figures 22C, 22D, 23:
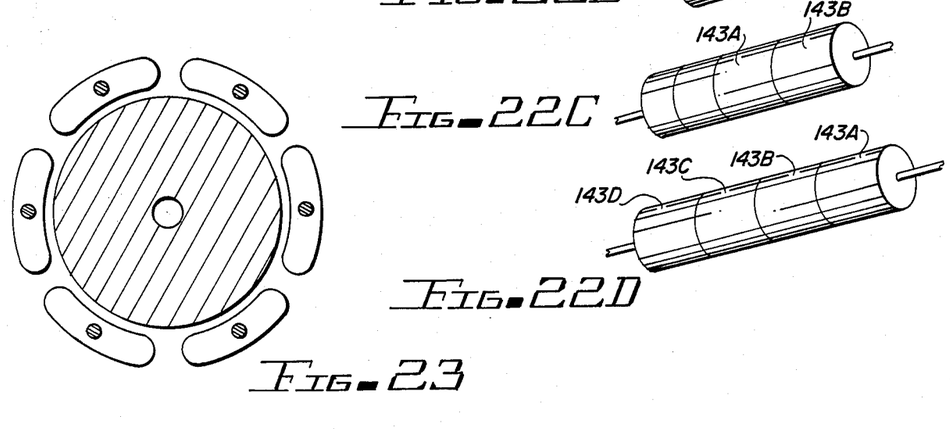
FIG. 23 is a section view useful in describing another embodiment of the invention.

Control system 139 controls the amount of expansion of each DLA cell 123, 124, 125, etc. Each of the minor DLAs in DLA assemblies 131, 132, etc., has a configuration of, and operates in the manner indicated in FIGS. 22A-22D. That is, each includes a plurality of DLA cells such as 143, each of which can forcefully expand or contract a predetermined amount, in the manner previously described. For example, in FIG. 22B only one of the DLA cells 143A has expanded. In FIG. 22C, two of the cells 143A and 143B have expanded, the two remaining ones remaining in their contracted configuration. But finally, in FIG. 22D, all of the cells 143A-143D are expanded.

Returning to FIG. 19, it can be seen that the above structure can effectuate forceful "axial" expansion or contraction, in relatively large increments corresponding to the expansion/contraction distance of each of the major DLA cells 123, 124, etc., in the direction indicated by arrows 135. Any time one or more of the major DLA cells is actuated, each of the minor DLA cells in each of the minor DLA assemblies 131, 132, etc., must be actuated to produce the same amount of expansion or contraction. Then, no rocking or pivoting of the snake arm 121 will occur. If it is desired to cause the distal or outward end of snake arm 121 to pivot in the direction indicated by arrows 137, corresponding and precise contraction and expansion of the correct number of minor DLA assemblies 131 and 133 must be effectuated by control system 139.

If it is desired to make the end of snake arm 121 swing in the directions indicated by arrows 136, appropriate and corresponding precise actuation of minor DLAs in minor DLA assemblies 132 and 134 must be effectuated by control system 139. A bit of further reflection on the possible operating modes of snake arm 121 will lead one to realize that the snake arm 121, if it is long enough, can be made to expand outward, and extend around corners, through curved tunnels, and the like, if the proper information regarding the desired path and configuration of snake arm 121 is made available to control system 139.

Figures 20, 20A:
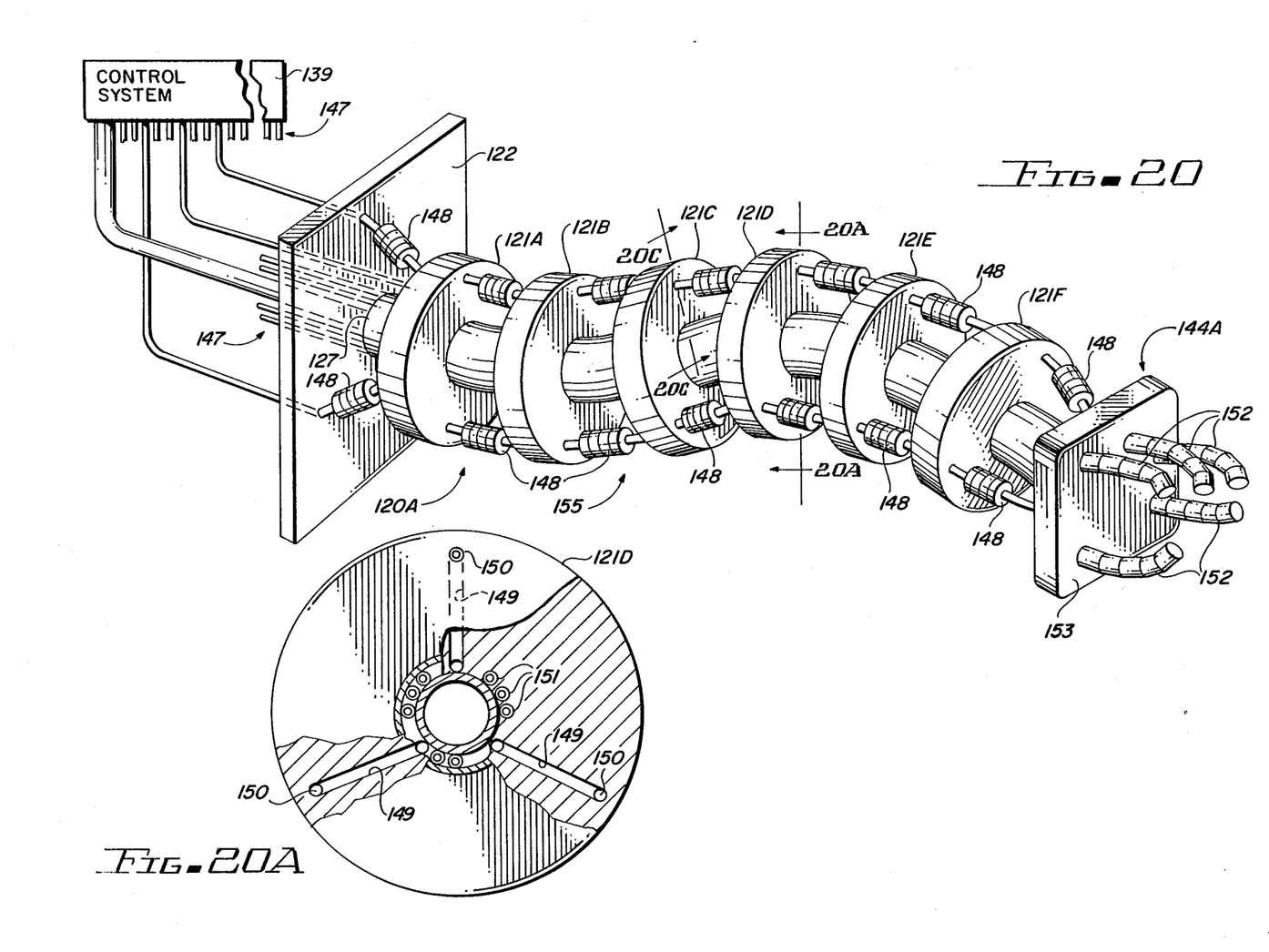
FIG. 20 is a perspective view of an alternate embodiment of a snake-like digital linear actuator arm in accordance with the present invention.
FIG. 20A is a section view taken along section line 20A—20A of FIG. 20.

Referring next to FIGS. 20, 20A, and 20B, an alternate, perhaps more practical embodiment of the invention shown in FIG. 19 is disclosed. The control system and stationary plate are essentially the same as in FIG. 19. The major DLA cells 121A-F are the same as the major DLA cells in FIG. 19. The flexible connecting elements 127 are the same as in FIG. 19. However, the cables 130 have been omitted, as have the minor DLA assemblies 131. Instead, at least three peripheral minor DLAs 148 are pivotally, peripherally attached to three points of each major DLA cell, attaching it to the previous DLA cell. In the case of DLA cell of major DLA cell 121A, the three minor DLAs 148 connect three peripheral points thereof to the stationary support plate 122.

Each of the minor DLAs 148 can be pneumatically powered. Each is capable of forceful, incremental expansion or forceful, incremental contraction. Pressurized fluid can be provided to power each of the minor DLA cells of each minor DLA 148 by means of channels 149, as shown in FIG. 20A, connecting the minor DLA cells to the same power supply or source of pressurized fluid as the major DLA cells 121A, 121B, etc. Either pneumatic or electrical control cables such as 151 in FIG. 20A can be routed to the individual minor DLA cells. Reference numeral 147 in FIG. 20 indicates (in a generalized fashion) control cables or tubes that are necessary to effectuate responsive control of each major DLA cell and each minor DLA cell in order to produce the desired snake-like movement of snake arm 155.

In FIG. 20, reference numeral 144 designates a utilization mechanism, which includes a support plate having a pivot hand 145 attached to it and controlled by two minor DLAs 148 connected between the support plate and the previous major DLA cell 121F. Utilization device 144 includes five flexible DLA "fingers" 152, each having a controlled "end effector" or other utilization device connected to its outer end. Each of the fingers 152 is a structure that is essentially similar to, but smaller than, snake arm 155.

Figure 21:
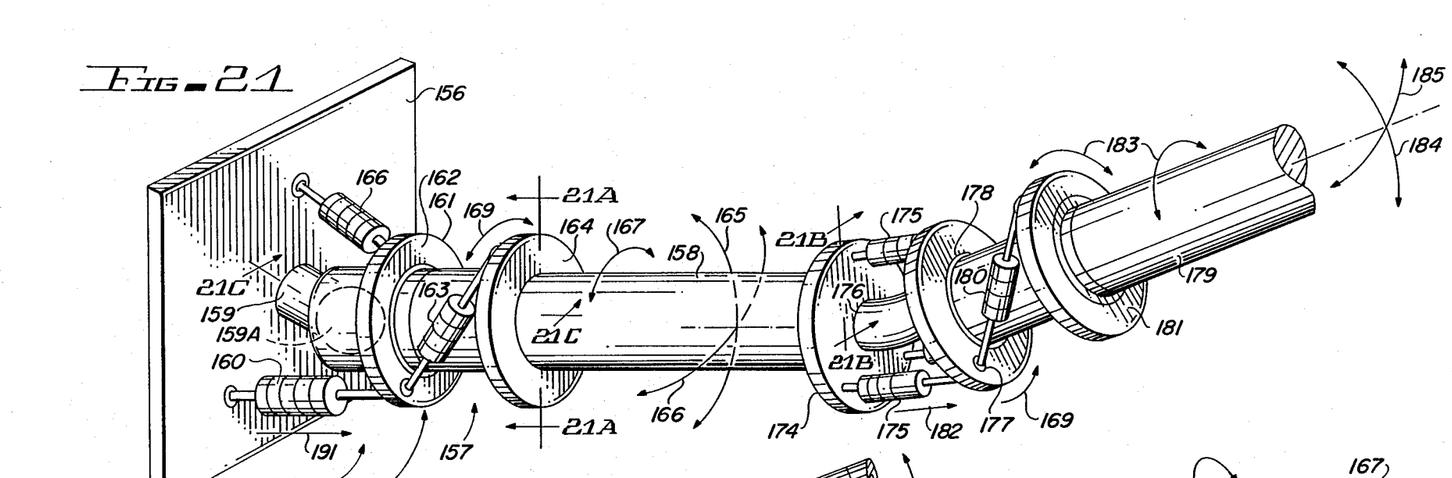
FIG. 21 is a partial perspective view of an alternate digital linear actuator device that can simulate the movement of a human shoulder and arm.

Referring next to FIG. 21, in articulated robotic device 154 is disclosed which performs functions analagous to the functions of a human shoulder, upper arm, elbow, and lower arm. The device 154 includes a base plate 156 having a stud 159 with a ball 159A attached thereto. A first arm 158 has a socket at its left end into which the ball 159A fits, so that arm 158 can pivot in any of the directions indicated by arrows 165 and 166.

Although not shown in FIG. 21, it should be appreciated that plate 156 need not be stationary, and can be attached by peripheral DLAs to another plate which in turn can be moved vertically and horizontally within its plane to more precisely approximate the movement of a human shoulder. The peripheral DLAs referred to could cause the plate 156 to tilt in a predetermined fashion, similar to the manner in which a human shoulder can tilt, and be moved forward, backward, up, and down.

Arm 158 extends through a bearing 162 that is supported by a ring plate 161. The peripheral portions of ring plate 161 are pivotally attached to one end of each of at least three DLAs 160, the opposite ends of which are pivotally attached to the plate 156. This arrangement allows arm 158 to rotate with respect to ring plate 162, and also allows precise pivoting of arm 158 by actuating one or more of the digital linear actuators 160 to tilt ring plate 162.

A ring plate 164 is rigidly attached to arm 158 and is spaced to the right from ring plate 161. Two digital linear actuators 163 (see also FIG. 21A) each are inclined relative to the plane of ring plate 164 and have their ends pivotally connected to peripheral portions of ring plates 162 and 164 respectively. Thus, for example, when the DLAs 163 are expanded as indicated by arrows 173 in FIG. 21A, rotation of ring plate 164 in the direction of arrows 170 of FIG. 21A occurs, thereby causing arm 158 to rotate in the same direction as ring plate 164. Bearing 162 permits such rotation. Contraction of the DLAs 163 causes rotation of ring plate 164 and arm 158 in the opposite direction. Thus, arrows 167, 169, 165, and 166 show the various degrees of freedom that the above structure provides to arm 158.

Figure 21A:
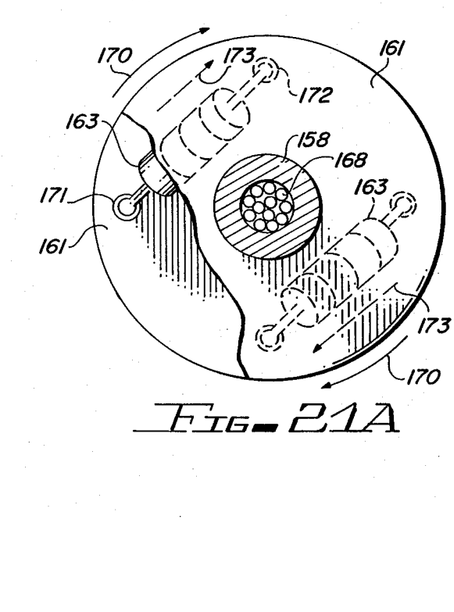
FIG. 21A is a section view taken along section line 21A—21A of FIG. 21.
Figure 21B:
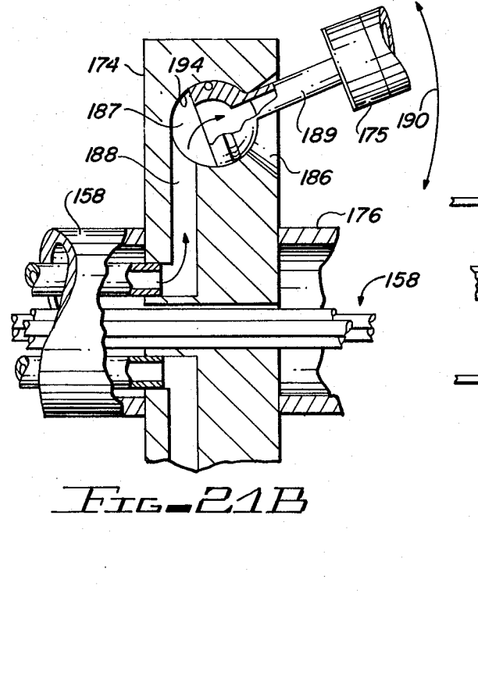
FIG. 21B is a partial section view taken along section line 21B—21B of FIG. 21.

In FIG. 21A, reference numeral 168 designates pneumatic conductors and/or electrical cables which supply compressed fluid and/or control signals to the DLAs 160 and 163 described above, and also to DLAs 175 and 180, subsequently described. The partial section view of FIG. 21B illustrates how air passages such as 188 are provided in the ring plate 174 which is attached rigidly to the distal end of arm 158 and provides compressed air to actuate digital linear actuator 175 through a ball and socket arrangement including a spherical ball 187 disposed in a sealed manner in a socket 194 and through a tubular connection 189 to the DLA 175. A generally conical cut-out 186 provides a wide pivoting angle for the DLA relative to the plane of ring plate 174, as indicated by arrows 190.

Figure 21C:
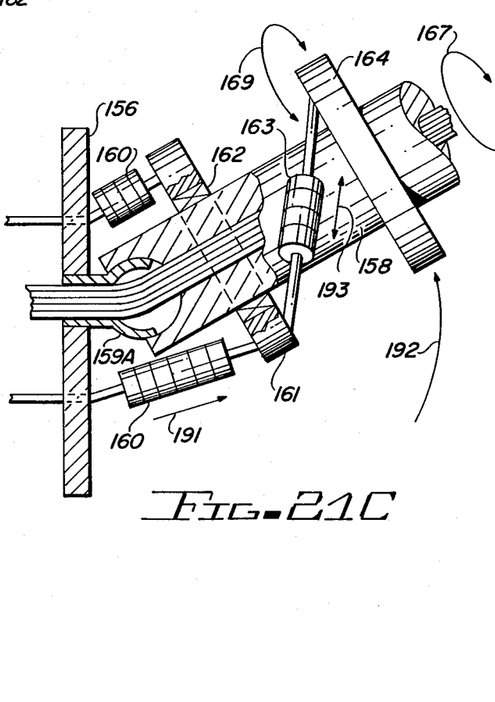
FIG. 21C is a partial section view along section line 21C—21C of FIG. 21.

Referring again to FIG. 21, a flexible coupling 176 is provided between end plate 174 and the left end of a second arm 179. This flexible coupling can be similar to those previously discussed in that it is resistant both to compression and contraction yet allows pivoting. At least three DLAs 175 are peripherally, pivotally connected to connection points of end plate 174 and corresponding connection points of ring plate 177. Ring plate 177 is supported on a bearing 178 through which arm 179 extends, similarly to the previously described structure of ring plate 161 and bearing 162. Ring plate 181 is rigidly attached to arm 179. As before, a pair of DLAs 180, inclined to the plane of ring plate of 181, are pivotally, peripherally connected to ring plate 177 and 181 to effectuate rotation of ring plate 181 and arm 179 in the directions indicated by arrows 183. This arrangement also provides pivoting of arm 179 in the directions indicated by arrows 184 and 185. This structure is also shown in the partial section view of FIG. 21C.

While the invention has been described with reference to several particular embodiments thereof, those skilled in the art will be able to make various modifications to the described embodiments of the invention without departing from the true spirit and scope thereof. It is intended that elements of the disclosed embodiments of the invention which are equivalent to those disclosed herein in the sense that the perform substantially the same function in substantially the same way to achieve the substantially the same result are to be encompassed within the scope of the invention.

For example, other media for causing expansion of the inner expansion chamber than those described can be used. Magnetic media, in the form of a magnetic field produced by a solenoid can be used, so that a digital linear (or non-linear) actuator can be constructed by a plurality of solenoid mechanisms connected end-to-end, and each controlled in response to a respective digital signal.

I claim:
1. A digital actuator comprising:
   (a) a plurality of digital actuator cells, each digital actuator cell having an axis of expansion and first and second end surfaces, each digital actuator cell including:
      i. outer means for expanding or contracting along the axis of that digital actuator cell, and having first and second end surfaces on opposed ends of the outer means,
      ii. inner means disposed within the outer means for expanding or contracting along the axis, and having first and second end surfaces, on opposed ends of the inner means,
      iii. means responsive to a digital control signal for causing a medium in the inner means to cause the inner means to expand a predetermined amount in the direction of the axis of that digital actuator cell in response to a first binary level of the digital control signal and for allowing a contraction of the inner means to its initial dimension in response to a second binary level of the digital control signal, and
      iv. first connecting means for connecting the first end surface of the inner means in fixed relationship to the end surface of the outer means that is located on the opposite side of the inner means, and second connecting means for connecting the second end surface of the inner means in fixed relationship to the other end surface of the outer means, wherein expansion of the medium in the inner means causes a predetermined amount of expansion of the inner means along the axis of that digital actuator cell and a predetermined amount of contraction of the outer means along the axis; and
   (b) a plurality of third connecting means, each for connecting the first end surface of one digital actuator cell to the second end surface of an adjacent actuator cell, the plurality of digital actuator cells being connected in series by respective ones of the third connecting means to form the digital linear actuator.

2. The digital actuator of claim 2 wherein the medium is a gas.

3. The digital actuator of claim 2 wherein in each digital actuator cell the outer means includes a first housing which includes the first end surface and a side surface which define a first volume, and wherein the outer means also includes a second housing which includes the second surface and a side surface defining a second volume and having an open end, the first housing extending in telescoping fashion into the second housing.

4. The digital actuator of claim 3 wherein in each digital actuator cell the inner means includes a piston disposed movably in the first volume, the wall of the piston engaging inner surfaces of the side wall of the first housing in sealed relationship therewith, the inner means having an end covered by an end plate, and wherein the first connecting means includes a piston rod connected to the piston and extending through a hole in the end plate in sliding, sealed relationship thereto and connected in fixed relationship to the second end surface, of the outer means and wherein the second connecting means includes means for connecting the periphery of the end plate to the side wall of the first housing.

5. The digital actuator of claim 4 wherein in each digital actuator cell the piston rod includes a passage extending therethrough for conducting pressurized gas into an inner expansion region between the end plate and the piston, and wherein the expansion causing means includes first valve means for opening and closing in response to the digital control signal to control passage of pressurized gas through the piston rod into the inner expansion.

6. The digital actuator of claim 5 wherein in each digital actuator cell the third connecting means includes a flexible tube having an opening extending therethrough in open communication with the passage through the piston rod for effectuating passage of pressurized gas from an adjacent digital actuator cell into the passage through the piston rod.

7. The digital actuator of claim 1 wherein each of the digital actuator cells has the same predetermined amount of contraction in response to the first binary level of the digital control signal applied to that digital actuator cell, whereby the digital actuator is a digital linear actuator.

8. The digital actuator of claim 1 wherein various different ones of the digital actuator cells contract different predetermined amounts in response to the first binary levels of the digital control signals respectively applied thereto, whereby the digital actuator is a digital non-linear actuator.

9. The digital actuator of claim 1 wherein the digital control signals respectively applied to the plurality of digital actuator cells are electrical signals.

10. The digital actuator of claim 1 wherein the digital control signals applied to the respective digital actuator cells are fluid signals, the digital actuator also comprising means for conducting the fluid signals.

11. The digital actuator of claim 1 including control means for producing the plurality of digital signals in response to a signal determinative of the desired amount of contraction of the digital actuator.

12. The digital actuator of claim 6 wherein each digital actuator cell includes second valve means for opening and closing in response to the digital control signal to control venting of pressurized gas out of the inner expansion region to effectuate relaxing of that digital actuator cell.

13. The digital actuator of claim 12 wherein each digital actuator cell includes means for actuating the first and second valve means to prevent passage of pressurized gas into the inner expansion chamber and to prevent venting of pressurized gas out of the inner expansion region to thereby effectively lock that digital actuator cell in its present expanded or contracted configuration.

14. The digital actuator of claim 1 wherein the means for causing the medium to cause the inner means to expand a predetermined amount includes a solid substance contained in the inner means and further includes heating means responsive to the digital control signal and thermally contacting the solid substance for heating the solid substance to thereby cause the predetermined amount of expansion of the inner means.

15. The digital actuator of claim 14 further including cooling means thermally contacting the solid substance for cooling it and causing it to contract in response to the digital control signal.

16. The digital actuator of claim 15 wherein the heating means and the cooling means are comprised in a Peltier device.

17. The digital actuator of claim 12 wherein the pressurized gas has the property that it is explosive if ignited, and wherein in each digital actuator cell the first valve means includes an injector means for injecting a predetermined charge of the explosive pressurized gas into the inner expansion chamber in response to the digital control signal and further includes igniting means responsive to the first control signal for igniting the injected charge of the pressurized explosive gas to cause the predetermined amount of expansion of the inner expansion chamber, hence the predetermined amount of contraction of that digital actuator cell.

18. A digital actuator comprising a plurality of digital actuator cells connected in series, each of said digital actuator cells including two connection points, one at each end thereof, for effectuating connection to an adjacent digital actuator cell or to an external element to which a force is to be applied by the digital actuator, said digital actuator including a plurality of means for connecting the connection points of adjacent digital actuator cells together, each of said digital actuator cells including contracting means connected between the two connection points of that digital actuator cell for pulling those two connection points closer together by a precise predetermined distance in response to a corresponding digital control signal, the contracting means including internal means for expanding in response to the digital control signal, opposed means for moving further apart by the predetermined distance in opposite directions in response to the expanding, and means connected to the opposed means and the two connection points for pulling the two connection points closer together, the digital actuator including means for applying a plurality of digital control signals to each of the digital actuator cells, respectively.

19. A method of causing a predetermined amount of movement of a first mechanical element with respect to a second mechanical element, said method comprising the steps of:
(a) providing a digital actuator including a plurality of digital actuator devices connected in series, each of which has two connection points and the property that it contracts by pulling its two connection points closer together by a precise predetermined distance in response to a first binary signal level and relaxes to its initial configuration in response to a second binary signal level, contraction of each individual digital actuator device shortening the length of the digital actuator by the predetermined distance, and relaxation of each individual digital actuator device lengthening the digital linear actuator by the predetermined distance, each digital actuator device including internal means for expanding in response to the first binary signal level, opposed means for moving further apart by the predetermined distance in response to the expanding, and means connected to the opposed means and the two connection points for pulling the two connection points closer together;

(b) connecting first and second ends of the digital actuator to connecting points of the first and second mechanical elements, respectively;

(c) applying the first binary signal level to a first group of the digital actuator devices to cause each of them to contract, simultaneously expanding a medium in the internal means of one of the digital actuator devices in response to the first binary signal level, moving the opposed means apart in opposite directions by the predetermined distance, and pulling the connecting points of that digital actuator device closer together by the predetermined distance in response to the moving apart, the predetermined amount of movement between the connecting points of the first and second mechanical elements being equal to the predetermined distance multiplied by the number of digital actuator devices in the first group.

20. Apparatus for causing a predetermined amount of movement of a first mechanical element with respect to a second mechanical element, said apparatus comprising:

(a) a digital actuator including a plurality of digital actuator device connected in series, each of which has two consecutive points and the property that it contracts by pulling its two connection points closer together by a precise predetermined distance in response to a first binary signal level and relaxes to its initial configuration in response to a second binary signal level, contraction of each individual digital actuator device shortening the length of the digital linear actuator by the predetermined distance, and relaxation of each individual digital actuator device lengthening the digital linear actuator by the predetermined distance, each digital actuator device including for expanding in response to the first binary signal level, opposed means for moving further apart by the predetermined distance in opposite directions in response to the expanding, and means connected to the opposed means and the two connection points for pulling the two connection points closer together in response to the moving apart;

(b) means for connecting first and second ends of the digital actuator to connecting points of the first and second elements, respectively; and (c) means for applying the first binary signal level to a first group of the digital actuator devices to cause each of them to contract, the predetermined amount of movement between the connecting points of the first and second mechanical elements being equal to the predetermined distance multiplied by the number of digital actuator devices in the first group.

21. An apparatus for causing a predetermined amount of movement of a first mechanical element in a desired direction with respect to a second mechanical element, the apparatus comprising:

(a) a major digital actuator including a plurality of major digital actuator cells connected in series, each of the major digital actuator cells having the property that it contracts a precise first predetermined distance in response to one binary signal level and returns to its initial configuration in response to an opposite binary signal level, contraction of each individual major digital actuator cell shortening the length of the major digital actuator by the first predetermined distance and the returning of each individual actuator cell having the effort of lengthening the major digital actuator by the first predetermined distance;

(b) means for connecting first and second ends of the major digital actuator to connecting points of the first and second mechanical elements, respectively;

(c) means for applying the binary signal level to a first group of the major digital actuator cells to cause each of them to contract, the predetermined amount of movement between the connecting points of the first and second mechanical elements being equal to the predetermined distance multiplied by the number of major digital actuator devices in the first group;

(d) a plurality of connecting means for pivotally connecting each of the major digital actuator cells to the next;

(e) a plurality of minor digital actuators each including a plurality of minor digital actuator cells connected in series, each minor digital actuator cell being similar to, but substantially smaller in size than, the major digital actuator cells, and each having the property that it contracts a precise second predetermined distance in response to one binary signal level and returns to its initial configuration in response to an opposite binary signal level, each of the minor digital actuators having one end connected to a peripheral portion of one of the major digital actuator cells and having another end connected to a corresponding peripheral portion of an adjacent major digital actuator cell, at least three of the minor digital actuators being connected between corresponding peripheral connecting points of each pair of adjacent major digital actuator cells, such that selective actuation of minor digital actuator cells of those three minor digital actuators pivots one of the major digital actuator cells relative to the other; and (f) means for controlling the binary signal levels to which each of the major digital actuator cells and each of the minor digital actuator cells respectively respond in order to effectuate snake-like movement of portions of said apparatus through a predetermined path.

* * * * *